United States Patent
Torben (10) Patent No.: US 10,548,333 B2
(45) Date of Patent: Feb. 4, 2020

(54) METHOD FOR PREPARING CAMEMBERT TYPE CHEESE (71) Applicant: CHR. HANSEN A/S, Hoersholm (DK)

(72) Inventor: Vindeloev Jannik Torben, Federiksberg C (DE)

(73) Assignee: CHR. HANSEN A/S, Hoersholm (DK)

( * ) Notice: Subject to any disclaimer, the term of this patent is extended or adjusted under 35 U.S.C. 154(b) by 710 days.

(21) Appl. No.: 15/035,408

(22) PCT Filed: Nov. 10, 2014

(86) PCT No.: PCT/EP2014/074199
§ 371 (c)(1),
(2) Date: May 9, 2016

(87) PCT Pub. No.: WO2015/067808
PCT Pub. Date: May 14, 2015

(65) Prior Publication Data
US 2016/0286830 A1 Oct. 6, 2016

(30) Foreign Application Priority Data

Nov. 11, 2013 (WO) .................. PCT/EP2013/073499

(51) Int. Cl.
A23C 19/068 (2006.01)
A23C 19/032 (2006.01)
C12R 1/46 (2006.01)
C12N 1/20 (2006.01)

(52) U.S. Cl.
CPC ...... *A23C 19/0682* (2013.01); *A23C 19/0323* (2013.01); *C12N 1/20* (2013.01); *C12R 1/46* (2013.01)

(58) Field of Classification Search
None
See application file for complete search history.

(56) References Cited

U.S. PATENT DOCUMENTS

| 4,205,090 A * | 5/1980 | Maubois ............ A23C 9/1422 426/36 |
| 4,919,944 A | 4/1990 | Bussiere |
| 2008/0050467 A1* | 2/2008 | Schlothauer ....... A23C 19/0323 426/2 |
| 2008/0171028 A1* | 7/2008 | Kringelum ............ A23C 9/123 424/93.45 |

FOREIGN PATENT DOCUMENTS

WO WO 2005/068982 A1 7/2005

OTHER PUBLICATIONS

Teuber et al., "The Genus Lactococcus" In The Prokaryotes, vol. 4, Dworkin, M. et al., Ed.; Springer Science+Business Media, LLC : Singapore; Chapter 1.2.7 (Year: 2006).*
Barrette, J. et al.; "The production of mixed cultures containing strains of *Lactococcus lactis, Leuconostoc cremoris* and *Lactobacillus rhamnosus*, on commercial starter media"; Journal of Industrial Microbiology & Biotechnology (2000) Dec. 25, 2000; pp. 288-297 Nature Publishing Group.
Mietton, B., et al.; "Minéraux et transformations fromagères" Chapter 16 in F. Gaucheron: Minéraux et produits laitiers; Nov. 1, 2003; Tec & Doc Lavoisier.
Kosikowski, et al.; Cheese and Fermented Milk Foods, vol. I, Origins and Principles, pp. i-ii; vol. II: Procedures and Analysis, pp. i-ii; Third Edition 1997; F.V. Kosikowski, L.L.C., Connecticut.
"Milk products—Determination of the acidification activity of dairy cultures by continuous pH measurement (CpH)"; ISO 26323, IDF 213, First edition, Jul. 1, 2009; pp. i-v, 1-13.
PCT International Search Report issued in application PCT/EP2014/074199 dated Apr. 13, 2015; 7 pages.

* cited by examiner

*Primary Examiner* — Michelle F. Paguio Frising
(74) *Attorney, Agent, or Firm* — Foley & Lardner LLP (57) ABSTRACT The present invention relates to a method for preparing a camembert type cheese using a well-defined starter culture.

14 Claims, 7 Drawing Sheets

Figure 5: experiment G. The effect of blending pure M (○) and pure A (□) on the shape of the acidification curve of the mix (Δ).

FIG 6

Figure 6: experiment I. The effect of blending pure M (○) and pure A (□) on the shape of the acidification curve of the mix (Δ).

FIG 7

Figure 7: experiment J. The effect of blending pure M (○) and pure A (□) on the shape of the acidification curve of the mix (Δ).

METHOD FOR PREPARING CAMEMBERT TYPE CHEESE

FIELD OF INVENTION

The present invention relates to a method for preparing a camembert type cheese with a direct vat set starter culture, and to a bacterial starter culture useable in the method.

BACKGROUND OF INVENTION

By concentrating the milk solids, lowering pH with lactic acid, removing sugar, and adding salt, cheese was traditionally a way to conserve milk for later consumption. Today, cheese is mainly appreciated for its organoleptic properties.

Conventional cheese making consist of three key steps: Coagulation (formation of a casein gel also called the curd), Drainage (the expulsion of whey from the curd), and Maturation (ripening of the curd into cheese).

During these steps, coagulants (such as rennet) are used to coagulate the milk, and starter cultures are used to lower pH and reduce sugar levels by transforming the milk lactose to lactic acid by fermentation, and provide enzymes for cheese ripening.

In camembert, it is well known that the balance between the rate of acidification and the rate of whey expulsion is essential to obtain the right cheese quality. Even slight imbalances will impact the texture, flavour and taste of the cheese. For a comprehensive review of the effect of acidification during coagulation, drainage, on cheese quality and ripening see B. Mieton et al.

Traditionally, camembert type cheeses are produced with undefined bulk starter cultures (starters of unknown strain composition, prepared locally at the dairy). The use of undefined bulk starter cultures has several drawbacks, e.g. lack of consistency and batch-to-batch variation, and the undefined starters may contain strains with undesired properties, such as resistance to antibiotics, pro-phages and production of allergens.

Several attempts have been made to replace the undefined bulk starters with well-defined cultures, especially DVS cultures, but without any commercial success, apparently because it has turned out to be impossible to provide a well-defined starter culture that is able to mimic the properties of the undefined starter cultures hitherto used (eg with respect to acidification curve, acidification time, and texture, flavour (eg bitterness) of the resulting cheese, etc).

Thus, there is still a need for a well-defined starter culture that can be used for the production of camembert type cheese.

SUMMARY OF INVENTION

It has surprisingly turned out that it is possible to provide a well-defined starter culture that is able to mimic the bulk starter cultures traditionally used, especially with respect to the specific acidification curve that is crucial for the production of camembert cheese.

The present inventor has revealed that the well-defined culture should contain several strains with different acidification characteristics. Surprisingly, the present inventor has found out that the starter culture should comprise—besides a bacterial culture that normally is found in a starter culture—a bacteria culture that is not able to grow in milk added 4% salt.

In accordance with the above surprising findings, the present invention relates in its broadest scope to a method for preparing a cheese, preferably a soft cheese (e.g. a cheese of the camembert type) comprising the steps:

Adding to a milk substrate
  a1) a bacteria culture of type M (a lactic acid bacteria culture that has a maximum acidification rate of more than or equal to 0.05 pH units per hour but less than 0.15 pH units per hour in B-milk);
  a2) a bacteria culture of type R (a lactic acid bacteria culture that has a maximum acidification rate of more than or equal to 0.40 pH units per hour in B-milk, and a maximum acidification rate of less than 0.05 pH units per hour in B-milk added 4% salt);
  a3) optionally a bacteria culture of type S (a lactic acid bacteria culture that has a maximum acidification rate of more than or equal to 0.40 pH units per hour in B-milk and has a maximum acidification rate of more than 0.05 pH units per hour in B-milk added 4% salt); and
  a4) a coagulant.

The present invention further relates to a lactic acid bacterial (LAB) culture comprising
  A1) a bacterial culture of type M (a lactic acid bacteria culture that has a maximum acidification rate of more than or equal to 0.05 pH units per hour but less than 0.15 pH units per hour in B-milk)
  A2) a bacterial culture of type R (a lactic acid bacteria culture that has a maximum acidification rate of more than or equal to 0.40 pH units per hour in B-milk, and has a maximum acidification rate of less than 0.05 pH units per hour in B-milk added 4% salt); and
  A3) optionally a bacterial culture of type S (a lactic acid bacteria culture that has a maximum acidification rate of more than or equal to 0.40 pH units per hour in B-milk and has a maximum acidification rate of more than 0.05 pH units per hour in B-milk added 4% salt).

Another aspect of the present invention relates to a cheese a cheese obtainable by the method of the invention.

DETAILED DISCLOSURE

In a first aspect, the present invention relates to a method for preparing a soft cheese (e.g. a cheese of the camembert type) comprising the steps:
  a) Adding to a milk substrate
    a1) a bacteria culture of type M (a lactic acid bacteria culture that has a maximum acidification rate of more than or equal to 0.05 pH units per hour but less than 0.15 pH units per hour in B-milk);
    a2) a bacteria culture of type R (a lactic acid bacteria culture that has a maximum acidification rate of more than or equal to 0.40 pH units per hour in B-milk, and a maximum acidification rate of less than 0.05 pH units per hour in B-milk added 4% salt);
    a3) optionally a bacteria culture of type S (a lactic acid bacteria culture that has a maximum acidification rate of more than or equal to 0.40 pH units per hour in B-milk and has a maximum acidification rate of more than 0.05 pH units per hour in B-milk added 4% salt); and
    a4) a coagulant.

Preferred embodiments of this first aspect are:
A method comprising the steps:
  a) Adding to a milk substrate
    a1) a bacteria culture of type M; and
    a2) a bacteria culture of type R; and
    a3) a bacteria culture of type S; and
    a4) a coagulant; and b) Separating the curd from the whey; and
c) Adding a mold culture to the curd.

A method of the first aspect, wherein the culture in a1) is added at a concentration in the range from 10E4 to 10E10 colony forming units (CFU) per liter milk substrate.

A method of the first aspect, wherein the culture in a2) is added at a concentration in the range from 10E4 to 10E10 colony forming units (CFU) per liter milk substrate.

A method of the first aspect, wherein the culture in a3) is added at a concentration in the range from 10E4 to 10E10 colony forming units (CFU) per liter milk substrate.

A method of the first aspect, wherein a least one of the cultures of types M, R and S is added in liquid, frozen or freeze-dried form.

A method of the first aspect, wherein at least two of the cultures of types M, R and S are added simultaneously to the milk substrate.

A method of the first aspect, wherein the cultures of types M, R and S (if added) are added in the form of direct vat set cultures.

A method of the first aspect, wherein the cultures of types M, R and S (if added) are added as a single culture, e.g. as a blend packaged in the same package.

A method of the first aspect, wherein the culture of type M comprises one, two, three or more strains.

A method of the first aspect, wherein the culture of type M comprises one, two, three or more strains of the species *Lactococcus lactis*.

A method of the first aspect, wherein the culture of type R comprises one, two, three or more strains.

A method of the first aspect, wherein the culture of type R comprises one, two, three or more strains of the species *Lactococcus lactis*.

A method of the first aspect, wherein the culture of type S comprises one, two, three or more strains.

A method of the first aspect, wherein the culture of type S comprises one, two, three or more strains of the species *Lactococcus lactis*.

A method of the first aspect, wherein the mold culture is selected from the group consisting of *Penicillium* species, such as *Penicillium camemberti* or *Penicillium candida*, *Geotrichum* species, such as *Geotrichum candidum*.

A method of the first aspect, wherein the coagulant is selected from the group consisting of: an aspartic protease; a chymosin of animal origin; a fermentation produced chymosin (such as CHY-MAX® (bovine) or CHY-MAX® M (camel)); a fungal protease, etc.

In the second aspect, the present invention relates to a lactic acid bacterial (LAB) culture
comprising
A1) a bacterial culture of type M (a lactic acid bacteria culture that has a maximum acidification rate of more than or equal to 0.05 pH units per hour but less than 0.15 pH units per hour in B-milk)
A2) a bacterial culture of type R (a lactic acid bacteria culture that has a maximum acidification rate of more than or equal to 0.40 pH units per hour in B-milk, and has a maximum acidification rate of less than 0.05 pH units per hour in B-milk added 4% salt); and
A3) optionally a bacterial culture of type S (a lactic acid bacteria culture that has a maximum acidification rate of more than or equal to 0.40 pH units per hour in B-milk and has a maximum acidification rate of more than 0.05 pH units per hour in B-milk added 4% salt).

Interesting embodiments of the second aspect are:
A culture of the invention comprising
  A1) a bacterial culture of type M; and
  A2) a bacterial culture of type R; and
  A3) a bacterial culture of type S.
A culture of the invention comprising
  A1) 5-90% of the culture of type M; and
  A2) 5-90% of the culture of type R; and
  A3) 0-90% of the culture of type S;
the ratio is calculated as CFU relative to the total CFU of the culture.
A culture of the invention comprising
  A1) 5-90% of the culture of type M; and
  A2) 5-90% of the culture of type R; and
  A3) 5-90% of the culture of type S;
the ratio is calculated as CFU relative to the total CFU of the culture.
A culture of the invention comprising from 10E8 to 10E12 cell forming units (CFU) of the culture of type M per g culture.
A culture of the invention comprising from 10E8 to 10E12 cell forming units (CFU) of the culture of type R per g culture.
A culture of the invention comprising which comprises from 10E8 to 10E12 cell forming units (CFU) of the culture of type S per g culture.
A culture of the invention, which is in liquid, frozen or freeze-dried form.
A culture of the invention, wherein the cultures of types M, R and S (if present) is a mixed culture in the same package.
A culture of the invention, wherein at least one of the cultures of types M, R and S (if present) is packaged as individually, e.g. as a kit-of-parts. Thus, the culture might be packaged and supplied to the customer in one, two, three or more separate packages.
A culture of the invention, wherein the culture of type M comprises one, two, three or more strains.
A culture of the invention, wherein the culture of type M comprises one, two, three or more strains of the species *Lactococcus lactis*.
A culture of the invention, wherein the culture of type R comprises one, two, three or more strains.
A culture of the invention, wherein the culture of type R comprises one, two, three or more strains of the species *Lactococcus lactis*.
A culture of the invention, wherein the culture in of type S comprises one, two, three or more strains.
A culture of the invention, wherein the culture of bacteria of type S comprises one, two, three or more strains of the species *Lactococcus lactis*.
A culture of the invention, wherein the concentration of bacteria is in the range of 10E9 to 10E13 CFU per g.
A culture of the invention, which is in frozen form.
A culture of the invention, which is in freeze dried form.
A culture of the invention, which is in liquid form.
A culture of the invention, which is in dried form.

In a third aspect, the present invention relates to a cheese obtainable by the method of the invention, and a cheese comprising a LAB culture of the invention. The cheese may be a camembert type cheese.

In a further aspect, the present invention relates to a method for acidifying a milk substrate by adding a culture of the invention to the milk substrate. The product of the process may be a fermented milk product ready for consumption, such as yoghurt, buttermilk, sour cream, etc, or the product may be further processed, e.g. by addition of an enzyme such as a coagulant. Such products are also a part of the present invention.

In the last aspect, the present invention relates to the use of a culture of the invention a process for producing cheese.

Definitions

In the present context, the term "soft cheese" or "camembert type cheese" refers to soft-ripened cheese such as camembert, brie, etc.

In the present context, the term "cheese" comprises soft cheese and hard or semi hard cheese, for example Cheddar, Red Leicester, American cheese, gouda, edam, emmental, an Italian cheese such as Parmesan, Parmigiano, Regiano, Grana Padano, Provolone, Pecorino, or Romano.

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp.

In the present context, the term "a culture of type M" (or "a culture of bacteria belonging to the group M") designates a lactic acid bacteria culture that has a maximum acidification rate of more than or equal to 0.05 pH units per hour but less than 0.15 pH units per hour in B-milk.

In the present context, the term "a culture of type S" (or "a culture of bacteria belonging to the group S") designates a lactic acid bacteria culture that has a maximum acidification rate of more than or equal to 0.40 pH units per hour in B-milk, but will not acidify B-milk added 4% salt (less than 0.05 pH units per hour). In the present context, "salt" is NaCl.

In the present context, the term "a culture of type R" (or "a culture of bacteria belonging to the group R") designates a lactic acid bacteria culture that has a maximum acidification rate of more than or equal to 0.40 pH units per hour in B-milk and acidify B-milk added 4% salt (i.e. having a maximum acidification rate of more than 0.05 pH units per hour).

It is understood that in the above definitions the culture is grown in B-milk (9.5% reconstituted skimmed milk heated to 99 C for 30 min) at 30 degrees C. The inoculation rate is not important, as the acidification rate is substantially the same when the milk is inoculated with from 10E2 to 10E10 CFU/ml milk. It is however preferred that the inoculation rate is 10E8 CFU/ml milk in the definitions. The term "culture" refers to a pure strain (a single strain) or a co-culture of pure strains, i.e. an ensemble of pure strains grown together. A strain should belong to a lactic acid bacterial species, preferably a *Lactococcus* species.

In the present context, the term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder. Preferably, at least part of the protein in the milk substrate is proteins naturally occurring in milk, such as casein or whey protein. However, part of the protein may be proteins which are not naturally occurring in milk. Prior to fermentation, the milk substrate may be homogenized and pasteurized according to methods known in the art.

The term "milk" is to be understood as the lacteal secretion obtained by milking any mammal, such as cows, sheep, goats, buffaloes or camels. In a preferred embodiment, the milk is cow's milk. The term milk also comprises soy milk. Optionally the milk is acidified, e.g. by addition of an acid (such as citric, acetic or lactic acid), or mixed, e.g. with water. The milk may be raw or processed, e.g. by filtering, sterilizing, pasteurizing, homogenizing etc, or it may be reconstituted dried milk. An important example of "bovine milk" according to the present invention is pasteurized cow's milk. It is understood that the milk may be acidified, mixed or processed before, during and/or after the inoculation with bacteria.

"Fermentation" in the methods of the present invention means the conversion of carbohydrates into alcohols or acids through the action of a microorganism. Preferably, fermentation in the methods of the invention comprises conversion of lactose to lactic acid.

Lactic acid bacteria are often supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product. Such cultures are in general referred to as "starter cultures" or "starters".

Processes for fermentation/acidification of a milk substrate, eg for the production of cheese, are well known and the person of skill in the art will know how to select suitable process conditions, such as temperature, oxygen, amount and characteristics of microorganism(s) and process time. Obviously, fermentation conditions are selected so as to support the achievement of the present invention.

In the present context, the term "mutant" should be understood as a strain derived from a strain of the invention by means of e.g. genetic engineering, radiation and/or chemical treatment, and/or selection, adaptation, screening, etc. It is preferred that the mutant is a functionally equivalent mutant, e.g. a mutant that has substantially the same, or improved, properties (e.g. regarding yield, viscosity, gel stiffness, mouth coating, flavor, post acidification, acidification curve, acidification, acidification speed, and/or phage robustness) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenisation step followed by a screening/selection step), but it is presently preferred that no more than 1000, no more than 100, no more than 20, no more than 10, or no more than 5, treatments are carried out. In a presently preferred mutant, less than 5%, or less than 1% or even less than 0.1% of the nucleotides in the bacterial genome have been changed (such as by replacement, insertion, deletion or a combination thereof) compared to the mother strain. In the present context, a mutant should be of the same type as the mother strain, ie a mutant of a mother strain of type M, R or S should also be of type M, R or S, resp.

In the present context, the term "variant" should be understood as a strain which is functionally equivalent to a strain of the invention, e.g. having substantially the same, or improved, properties e.g. regarding viscosity, gel stiffness, mouth coating, flavor, post acidification, acidification curve, acidification, acidification speed, and/or phage robustness). Such variants, which may be identified using appropriate screening techniques, are a part of the present invention. In the present context, a variant should be of the same type as the mother strain, i.e. variant of a mother strain of type M, R or S should also be of type M, R or S, resp.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

EXAMPLES

Example 1: pH Measurement Using the Method "Colour of pH"

Figure 1:
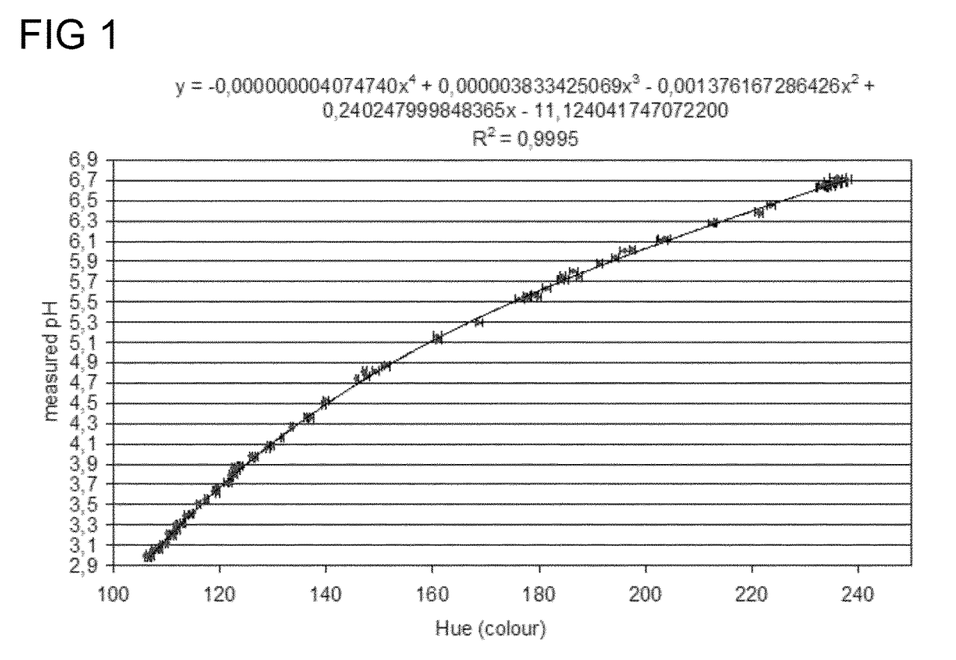
FIG. 1 depicts a Graph showing measured pH (vertical axis) as a function of colour (Hue) for flat bed scanner HP2401 (monile unit). Hue values are average±S.E. (n=4). The black line is a best fit 4th grade polynomium. The polynomium coefficients are printed on top of figure. The R2 correlation coefficient is also printed.

Materials
Transparent Nunc 96w plate (sterile)
Bromocresol purple (Aldrich)
Bromocresol green (Sigma)
Autoclaved demineralized H2O
0.2 um sterile filter
B-milk is Reconstituted Skimmed Milk (9.5%) heated to 99 C for 30 min. Cf. INTERNATIONAL STANDARD ISO26323, IDF213, First edition 2009-07-01: Milk products—Determination of the acidification activity of dairy cultures by continuous pH measurement (CpH).
Scanner for colour of pH (HP ScanJet 2400)
pH-meter (micro-electrode connected to the IQ50 pH meter (Scientific Instruments Inc., San Diego, USA))
Solutions
pH-indicator: 50 mg bromocresol purple salt (Aldrich) and 50 mg bromocresol green salt (Sigma) were dissolved in a final volume of 50 ml autoclaved demineralized H2O. The pH was adjusted to 7.0 with NaOH. The pH indicator was sterile filtered (0.2 µm) before use. pH-indicator milk: 95 ml B-milk was mixed with 5.0 ml pH indicator
Calibration
pH indicator milk was prepared with various amounts of Glucone-Delta-Lactone, in a 96 well plate, and pH was allowed to stabilize overnight at room temperature in the pH range 2.9 to 6.7. The color of the wells was measured using a flatbed scanner (HP Scanjet 2400) with appropriate scanner software (pH Multiscan v. 3.0) and pH in each well was measured with a suitable pH meter (e.g. Radiometer's or Metrohm's), allowing correlation between the measured pH and the color (Hue) of the wells. A plot with color (Hue, horizontal axis) vs. measured pH (vertical axis) was drawn and a best fit 4th grade polynomial was used to describe the curve: $pH = a*[Hue]^4 + b*[Hue]^3 + c*[Hue]^2 + d*[Hue] + e$. The coefficient of correlation was greater than 0.99 (FIG. 1). The 4th grade polynomial was then used to calculate the pH in wells of subsequent scans.

Example 2: Assay for Determination of Culture Type

Figure 2:
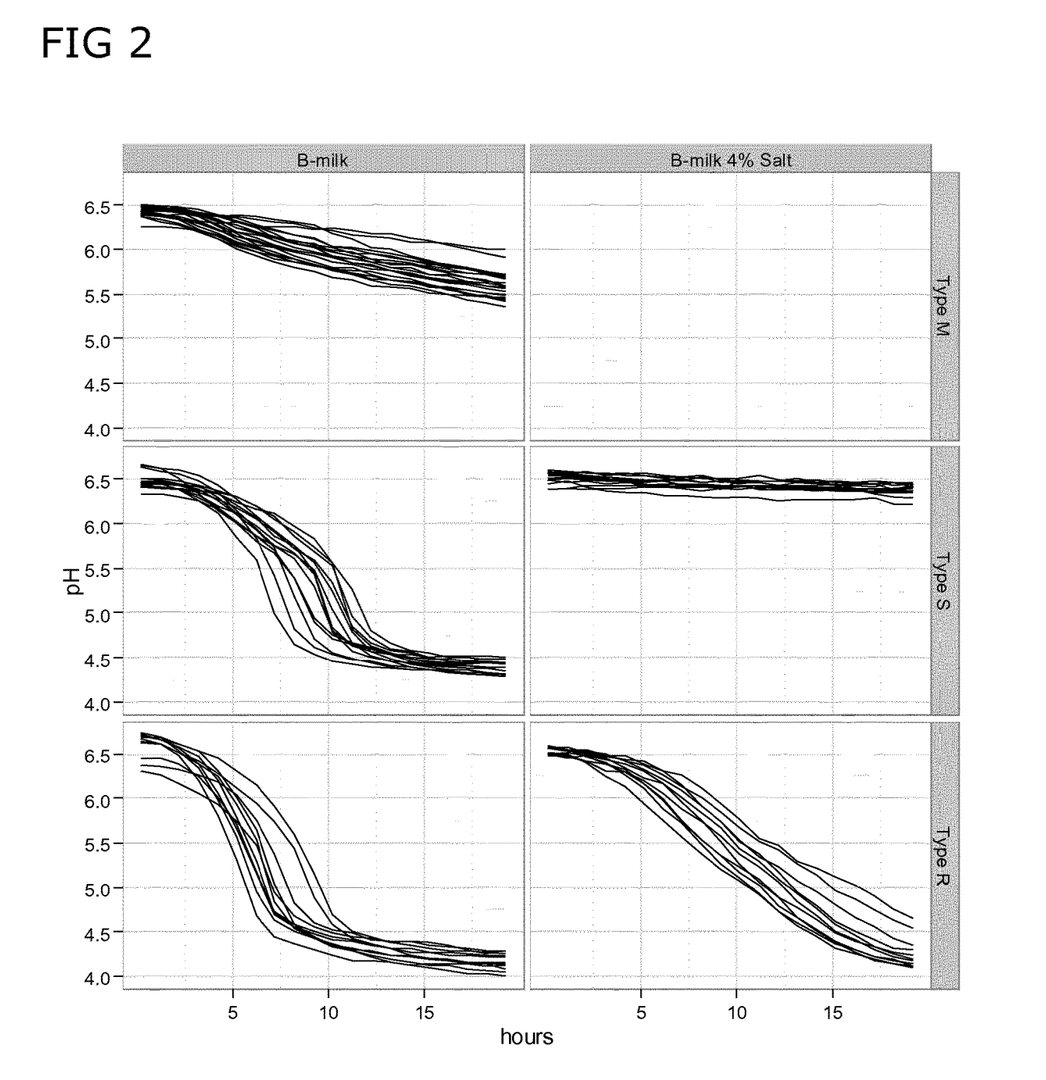
FIG. 2 depicts examples of the acidification of lactococcus cultures of type M (M1), S (S1), and R (R2) [as measured in microtiter plates using the colour of pH method]

This assay to be used to determine whether a culture is of any of type M, type S, or type R
Definition of cultures of types M, S and R:
It is understood that in the definitions the culture is grown in B-milk at 30 degrees C. In the following a "culture" refers to a pure strain (a single strain) or a co-culture of pure strains, i.e. an ensemble of pure strains grown together.
A culture of type M will have a maximum acidification rate of more than or equal to 0.05 pH units per hour but less than 0.15 pH units per hour in B-milk.
A culture of type S will have a maximum acidification rate of more than or equal to 0.40 pH units per hour in B-milk, but will not acidify B-milk added 4% salt (less than 0.05 pH units per hour).
A culture of type R will have a maximum acidification rate of more than or equal to 0.40 pH units per hour in B-milk and acidify B-milk added 4% salt (having a maximum acidification rate of more than 0.05 pH units per hour).
The pH can be measured using a conventional method, e.g. a pH electrode, or pH can be measured using Chr. Hansens proprietary method "colour of pH", see example 1 and WO2005068982A1.
Example on testing using the assay.
Materials:
M17-b: M17 (Oxoid CM 817): 37.25 g dissolved in 950 ml Millipore H2O, autoclaved for 20 min at 121° C., and dispensed 100 ml aliquots in sterile bottles.
M17-k (M17-broth+1% glucose+1% lactose): 100 ml M17-b is supplemented with 5 ml sterile glucose stock solution (20% w/v) and 5 ml sterile lactose stock solution (20% w/v)
Salt Milk (4% sodium): 100 ml pH indicator milk was added 5.3 g NaCl.
Cultures of bacteria to be tested were grown overnight in M17k media at 30 C. Strains of *Lactococcus lactis* were used as test cultures.
B-milk acidification: The overnight culture was added one percent to pH-indicator milk, and the pH measured every 6 minutes for 20 hours using a flatbed scanner as described in example 1.
Salt-milk acidification: The cultures were pre-incubated in B-milk and allowed to acidify for 2 hours after which they were transferred to Salt milk. pH measured by colour of pH is determined every 6th minute for 20 hrs. This protocol is part of the Primary characterization in the Strain supply chain.
Calculation of maximum acidification rates: The maximum acidification was calculated as the maximum change in pH observed between hourly pH measurements for a given pH curve, see FIG. 2.

Example 3: Controlling the Acidification Rate of Defined Direct to the Vat Cultures by Blending a Type M Culture with a Type S or Type R Culture 5 g per 100 L of a type M, R or S culture produced as a defined frozen direct vat set culture was added to semi skimmed milk (1.8% fat). Then 0, 2.5, 5, 10, 20, and 30, g per 100 L type M DVS culture was added.

Figure 3:
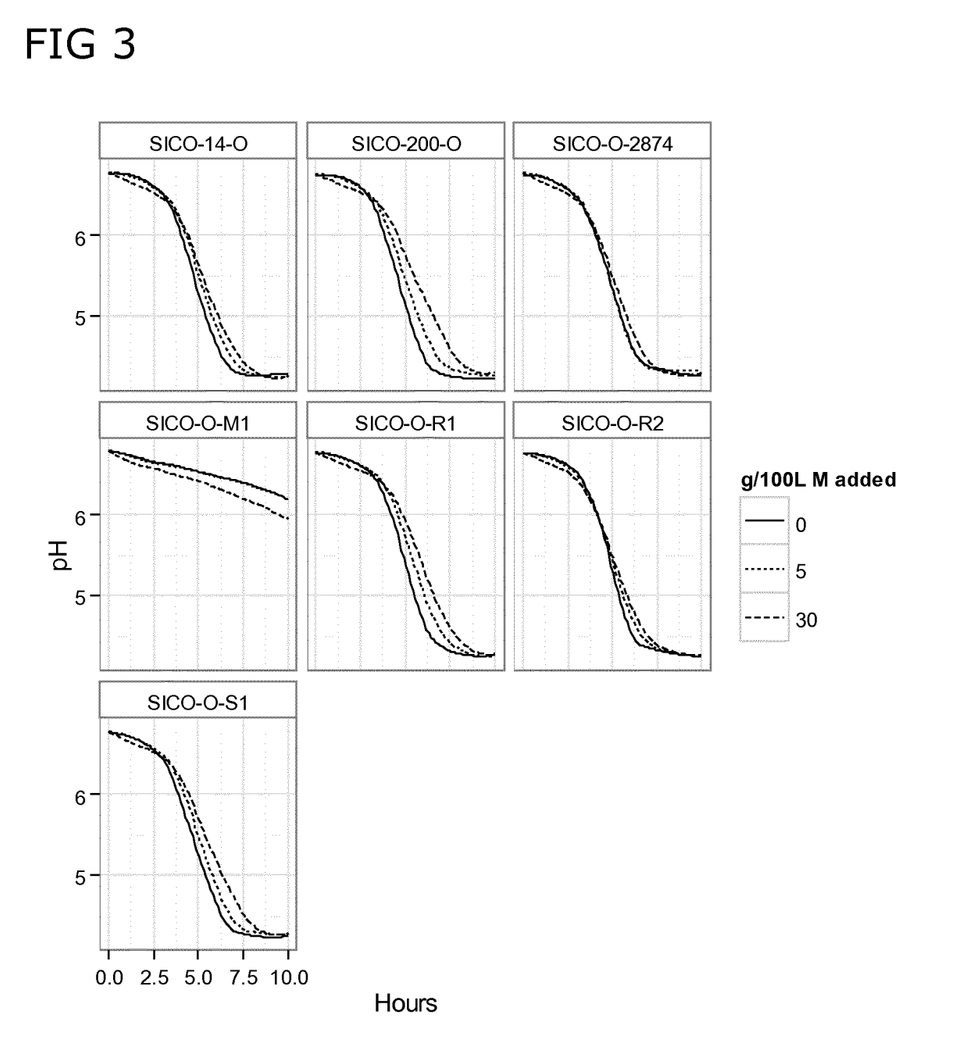
FIG. 3 depicts the effect of adding a type M culture to type S and R cultures. 5 g culture of the S or R type per 100 L was added 0, 5 and 20 g per 100 L M culture. Type S cultures: SICO-14-O, SICO-O-2874, and SICO-O-S1. Type R cultures: SICO-200-O, SICO-O-R1, and SICO-O-R2. Type M culture: SICO-O-M1

The pH was measured at least every hour for 10 hours to obtain a pH curve using the color of pH method (example 1) (see FIG. 3).

Figure 4:
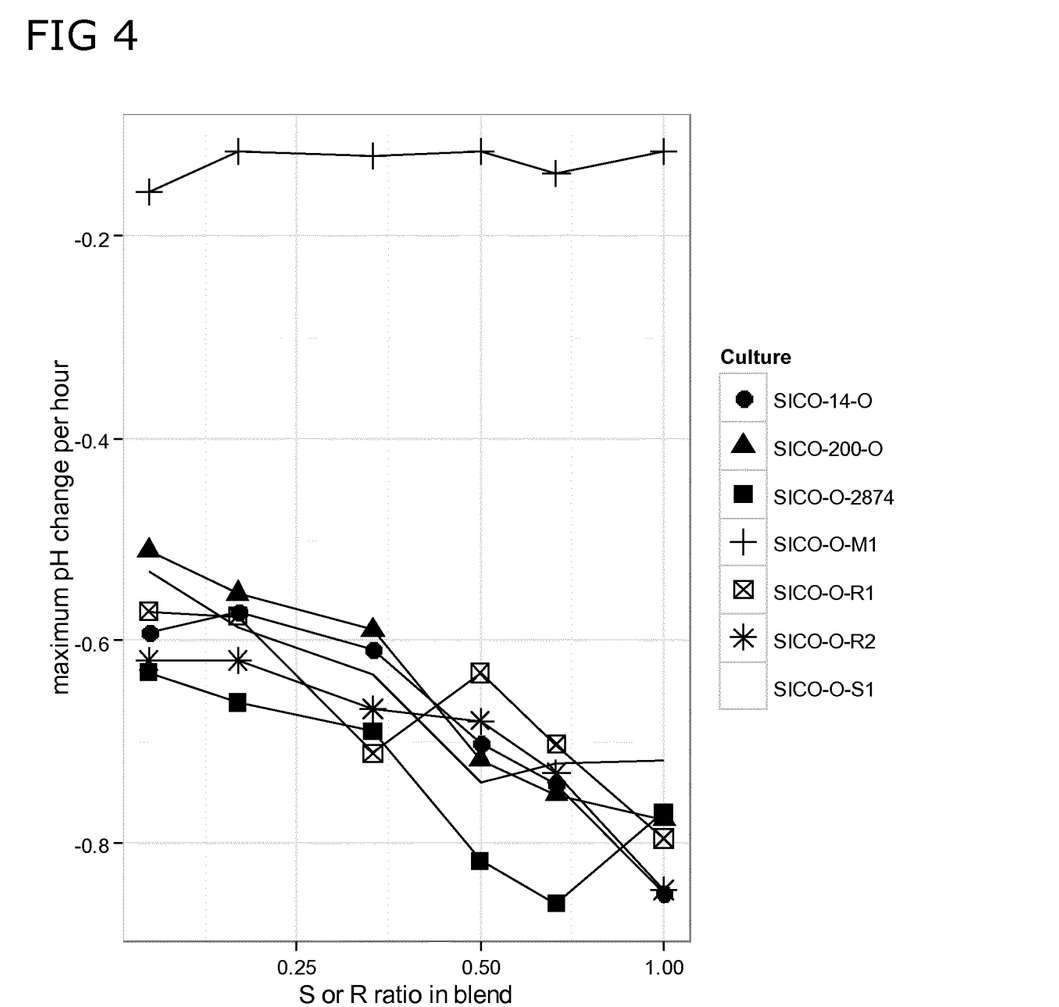
FIG. 4 depicts the maximum acidification rate as a function of the amount of type R or S culture in the type R+M or type M+S blends

When adding a type M culture to the type R and S cultures, the maximum acidification rate obtained were reduced (see FIG. 4). When adding type M culture to a type M culture, the maximum acidification rate was unchanged (see FIG. 4).

Example 4: Controlling the pH Slope of Blends

Materials and Methods:

A-milk is Reconstituted Skimmed Milk powder (9.5%) autoclaved at 115 C for 15 min.

B-milk is Reconstituted Skimmed Milk powder (9.5%) heated to 99 C for 30 min.

A suitable pH-meter giving the result with two digits (e.g. Radiometer's or Metrohm's) equipped with a pH electrode (e.g. a combination electrode from Radiometer (GK 2401C) or from Metrohm (6.0232.100)) and a thermometer for measuring the room temperature or a temperature sensor.

Experiment:

Overnight (o/n) cultures of each strain were prepared in A-milk at room temperature (20-24 C) in 200 ml sterile baby-bottles. The pH of each o/n culture was aseptically measured. The pH of the M-type strains was in the 5.5 to 5.8 range before use.

The pH of the R type strain was in the 4.5 to 4.6 range before use.

The o/n cultures were:
A) DSM 26564 in A-milk
B) DSM 26566 in A-milk
C) DSM 26569 in A-milk
D) DSM 26570 in A-milk The o/n cultures were then combined and inoculated as follows in 200 ml B-milk in baby-bottles:

Experiment G
G1) 1.5% (v/v) of B in B-milk (pure M type, DSM 26566)
G2) 0.1% (v/v) of A in B-milk (pure R type, DSM 26564)
G3) 1.5% (v/v) of B and 0.1% (v/v) of A in B-milk (mixed M and R type)

Experiment I
I1) 1.5% (v/v) of D in B-milk (pure M type, DSM 26570)
I2) 0.1% (v/v) of A in B-milk (pure R type, DSM 26564)
I3) 1.5% (v/v) of D and 0.1% (v/v) of A in B-milk (mixed M and R type)

Experiment J
J1) 1.5% (v/v) of C in B-milk (pure M type, DSM 26569)
J2) 0.1% (v/v) of A in B-milk (pure R type, DSM 26564)
J3) 1.5% (v/v) of C and 0.1% (v/v) of A in B-milk (mixed M and R type)

The single strains and blends (experiments G, I, and J) were then fermented at 30 C for 16 hours using a temperature controlled water bath. The pH was measured with a frequency of at least an hour using a suitable pH meter and electrode.

Figure 5:
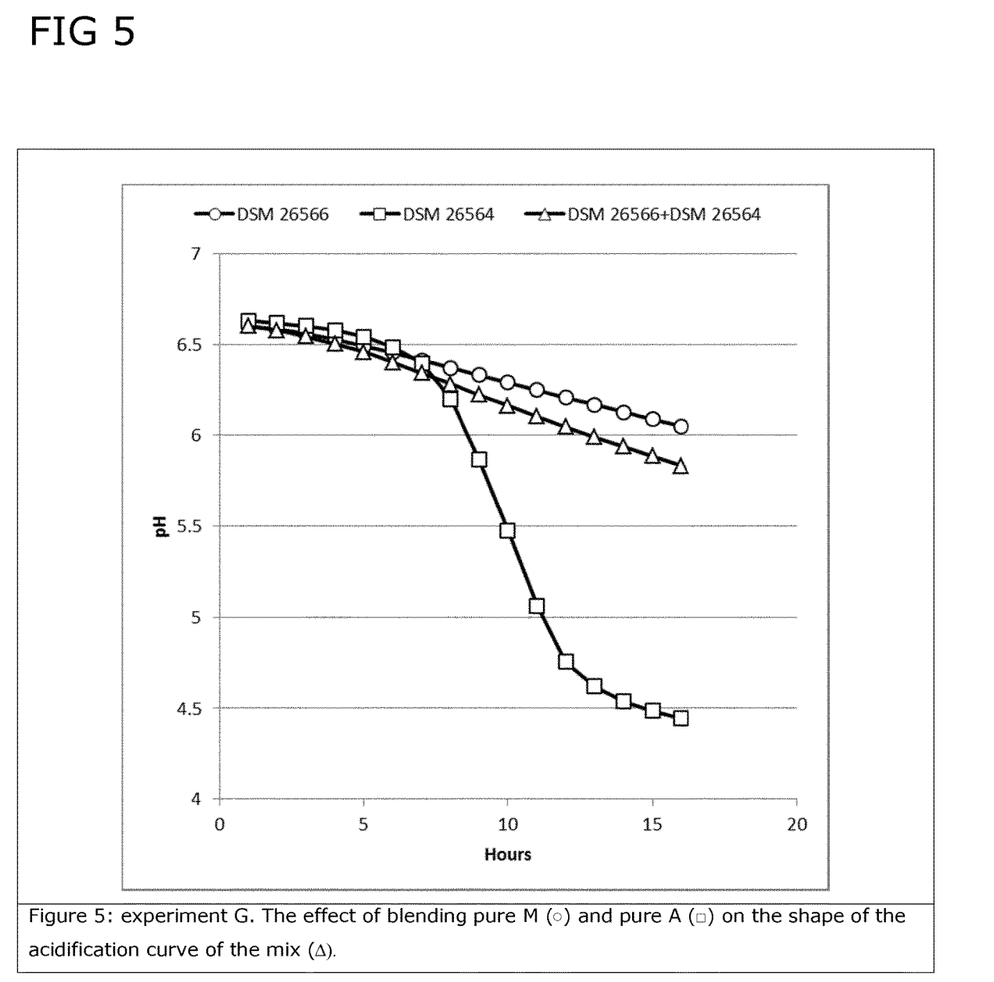
FIG. 5: The effect of blending pure M (○) and pure A (□) on the shape of the acidification curve of the mix (Δ). See experiment G in ex 4.
Figure 6:
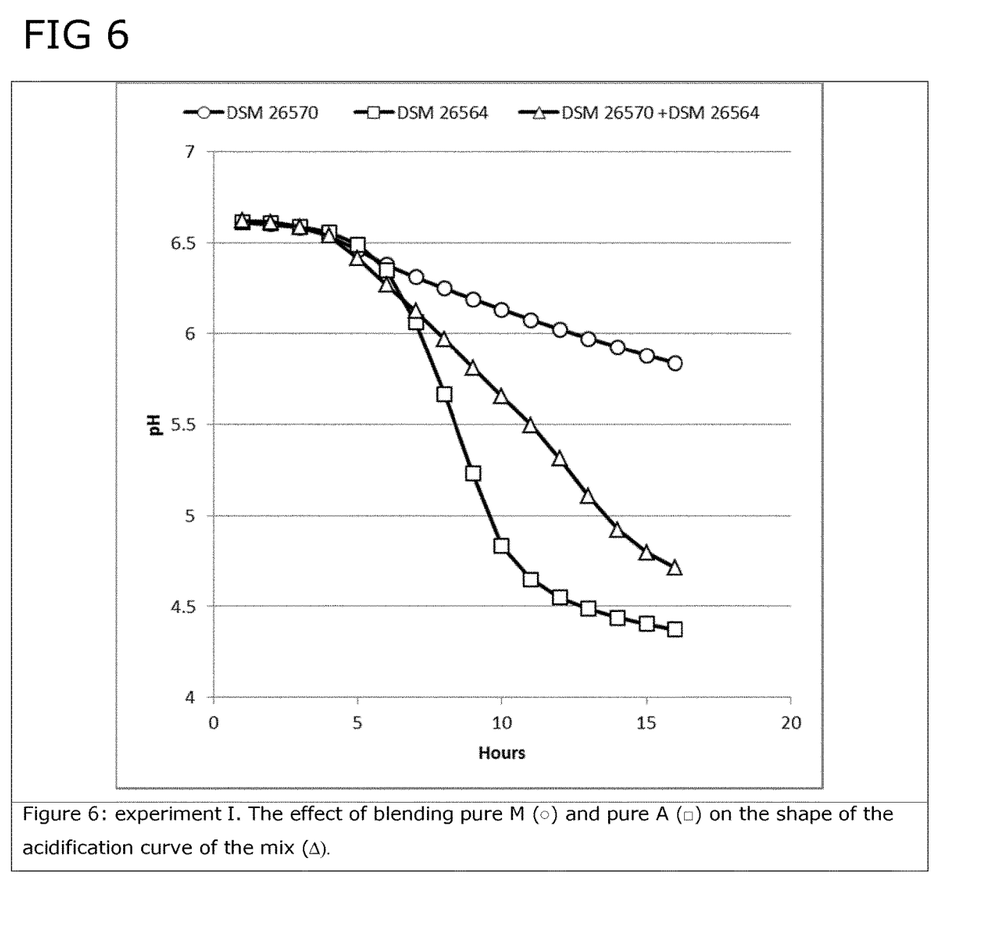
FIG. 6: The effect of blending pure M (○) and pure A (□) on the shape of the acidification curve of the mix (Δ). See experiment I in ex 4.
Figure 7:
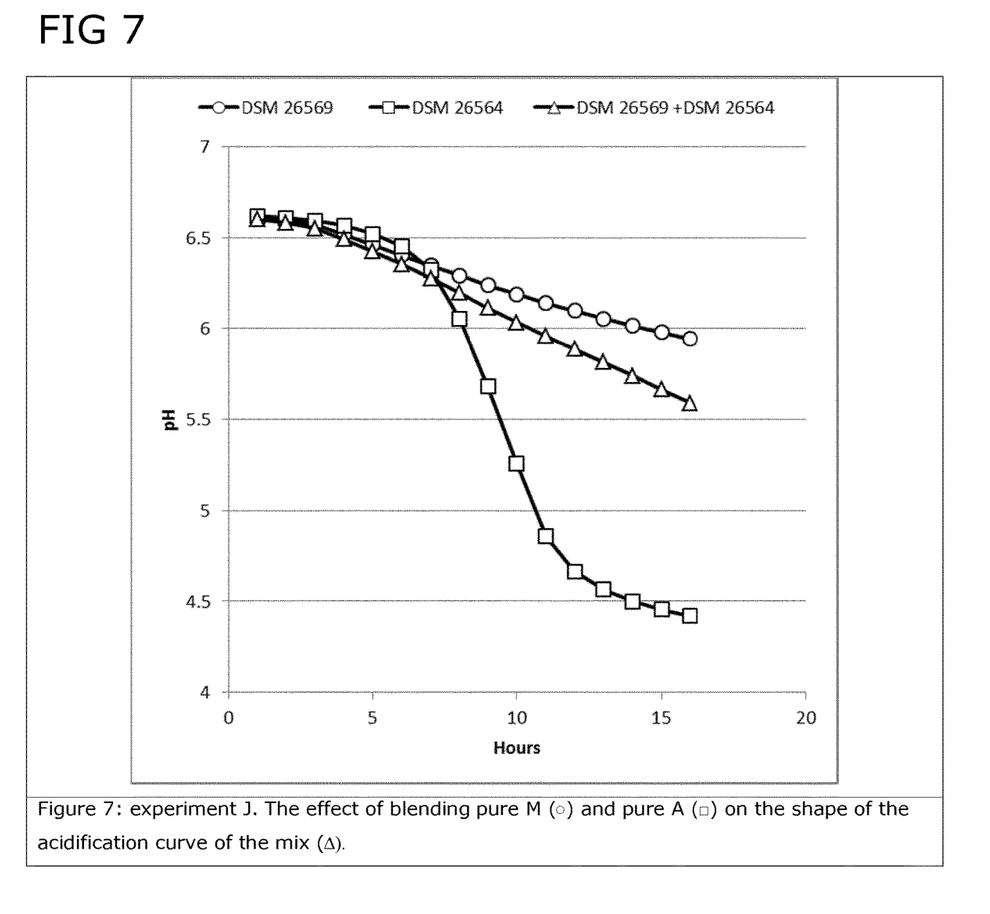
FIG. 7: The effect of blending pure M (○) and pure A (□) on the shape of the acidification curve of the mix (Δ). See experiment J in ex 4.

Results:

FIGS. 5 to 7 shows the effect of blending the same R strain ("Pure A") with three different M strains on the slope of the acidification curve. By combining different strain in various ratios the slope of the curve can be controlled.

Example 5: Production of Camembert Cheeses

Preparation of Starter Culture

Prepare o/n cultures A and D in A-milk from example 4 above.

Prepare a blend of A and D containing about 5% A and 95% D (Culture AD).

Centrifuge and freeze in liquid nitrogen.

First Pasteurization

Milk containing 3.74% protein and 3.5% fat is pasteurized at 73.5 C for 15 seconds and cooled to about 5 C First Maturation (Cold Physical and Biological Maturation)

The milk is added 20 ml CaCl2 solution (340 g/l) per 100 liter and 8 g of the frozen culture AD per 100 liter of milk and left to ferment for 15 to 17 hours at 14.5 C until pH 6.5 is reached.

Second Pasteurization

After reaching the target pH, the milk is then re-pasteurized at 73.5 C for 15 seconds and cooled to 34 C.

Secondary Maturation 3-5 units per 1000 L PCa 1 (*Penicilium candidum*) and 0.5-1 u GEO CD 1 per 1000 l (*Geotrichum candidum*) is added to the milk.

Finally, starter culture is added, 8 g of the frozen culture AD per 100 l, and left to ferment about an hour at 34 C until pH 6.30 is reached.

Renneting

At pH 6.3 about 20 ml of rennet (520 mg/l chymosin) is added to 100 liters of milk. After about 30 to 40 minutes at 34 C, the now formed curd is cut into 1 cubic cm cubes.

Stirring

The cubes are gently stirred after a couple of minutes.

Molding

When pH about 6.1-6.2 is reached the curd is transferred into industry standard camembert molds (11 cm in diameter) and left to drain.

Draining

The cheeses are drained at different temperatures: e.g. one hour at 27 C, two hours at 24 C, two hours at 20 C, and thereafter kept at 17 C just until de-molding.

During the draining step the molds are turned twice to facilitate draining: the first time one hour after the curd was filled into molds and then again after five hours.

De-Molding

After about seven hours after being filled into molds, the cheeses are released from the molds, dry salted by hand, and transferred to the ripening room.

Ripening

The cheeses are ripened at 14-15° C. and 85% relative humidity for one day, followed by 8-9 days at 10-13° C. and 95% relative humidity. When a satisfactory surface mold growth is obtained, the cheese surface is dried and stored at 4° C.

The cheese prepared as above have an acidification profile and mineral profile as a camembert cheese produced with a undefined bulk starter, and—compared to cheese made as above, but with a single strain culture A instead of the culture AD—a higher content of calcium and a longer shelf-life.

DEPOSITS AND EXPERT SOLUTION

The Applicant requests that a sample of the deposited microorganism should be made available only to an expert approved by the Applicant.

The Strains of the invention were deposited at Deutsche Sammlung von Mikroorganismen and Zellkulturen GmbH, Inhoffenstr. 7B, D-38124 Braunschweig (DSM) 31 Oct. 2012 and given the accession numbers as follows:

*Lactococcus lactis* ssp. *cremoris* CHCC4421=DSM 26561
*Lactococcus lactis* ssp. *lactis* CHCC9673=DSM 26563
*Lactococcus lactis* ssp. *lactis* CHCC10778=DSM 26564
*Lactococcus lactis* ssp. *lactis* CHCC11277=DSM 26565
*Lactococcus lactis* ssp. *cremoris* CHCC11552=DSM 26566
*Lactococcus lactis* ssp. *cremoris* CHCC11583=DSM 26567
*Lactococcus lactis* ssp. *cremoris* CHCC11603=DSM 26568
*Lactococcus lactis* ssp. *cremoris* CHCC12085=DSM 26569
*Lactococcus lactis* ssp. *cremoris* CHCC13347=DSM 26570

The deposits were made according to the Budapest treaty on the international recognition of the deposit of microorganisms for the purposes of patent procedure.

REFERENCES

B. Mieton, F. Gaucheron & F. Salaün-Michel: "Minéraux et transformations fromagères", chapter 16 in F. Gaucheron: "Minéraux et produits laitiers".
Cheese and Fermented Milk Foods, by Frank V. Kosikowski.
INTERNATIONAL STANDARD ISO26323 IDF213. First edition 2009-07-01: Milk products—Determination of the acidification activity of dairy cultures by continuous pH measurement (CpH)
WO2005068982A1

All references cited in this patent document are hereby incorporated herein in their entirety by reference.

The invention claimed is:

1. A lactic acid bacterial (LAB) culture comprising
   (A1) a lactic acid bacterial culture of type M that has a maximum acidification rate of more than or equal to 0.05 pH units per hour but less than 0.15 pH units per hour in B-milk, wherein the culture of type M comprises one or more *Lactococcus lactis* ssp. *cremoris* strains selected from CHCC11552 deposited at the Deutsche Sammlung von Mikroorganismen und Zellkulturen GmbH (DSMZ) in Braunschweig, Germany under accession number DSM 26566; CHCC11583 deposited at the DSMZ under accession number DSM 26567; CHCC11603 deposited at the DSMZ under accession number DSM 26568; CHCC12085 deposited at the DSMZ under accession number DSM 26569; CHCC13347 deposited at the DSMZ under accession number DSM 26570, and mutants thereof;
   (A2) a lactic acid bacterial culture of type R that has a maximum acidification rate of more than or equal to 0.40 pH units per hour in B milk, and has a maximum acidification rate of less than 0.05 pH units per hour in B-milk added 4% salt, wherein the culture of type R comprises one or more *Lactococcus lactis* ssp. *lactis* strains selected from CHCC10778 deposited at the DSMZ under accession number DSM 26564; CHCC11277 deposited at the DSMZ under accession number DSM 26565, and mutants thereof; and
   (A3) optionally, a lactic acid bacterial culture of type S that has a maximum acidification rate of more than or equal to 0.40 pH units per hour in B-milk and has a maximum acidification rate of more than 0.05 pH units per hour in B-milk added 4% salt wherein the culture of type S comprises one or more of *Lactococcus lactis* ssp *cremoris* strain CHCC4421 deposited at the DSMZ under accession number DSM 26561 *Lactococcus lactis* ssp. *lactis* strain CHCC9673 deposited at the DSMZ under accession number DSM 26563, and mutants thereof.

2. A LAB culture according to claim 1, comprising:
   (A1) 5-90% of the culture of type M; and
   (A2) 5-90% of the culture of type R; and
   (A3) 0-90% of the culture of type S;
   based on the total colony forming units (CFU) of the bacteria in the culture.

3. A LAB culture according to claim 1, comprising:
   (A 1) 60-98% of the culture of type M; and
   (A2) 1-20% of the culture of type R; and
   (A3) 1-20% of the culture of type S;
   based on the total colony forming units (CFU) of tile bacteria in the culture.

4. A LAB culture according to claim 1, comprising:
   (A1) 5-90% of the culture of type M; and
   (A2) 5-90° % of the culture of type R; and
   (A3) 5-90% of the culture of type S;
   based on the total colony forming units (CFU) of the bacteria in the culture.

5. A LAB culture according to claim 1, comprising from $10^8$ to $10^{12}$ colony forming units (CFU) of the culture of type M per gram culture.

6. A LAB culture according to claim 1, comprising from $10^8$ to $10^{12}$ colony forming units (CFU) of the culture of type R per gram culture.

7. A LAB culture according to claim 1, comprising from $10^8$ to $10^{12}$ colony forming units (CFU) of the culture of type S per gram culture.

8. A LAB culture according to claim 1, in liquid, frozen or freeze-dried form.

9. A LAB culture according to claim 1, the culture of type M, the culture of type R, and the culture of Type S.

10. A method for manufacture of a LAB culture according to claim 1, comprising:
(A) selecting a lactic acid bacteria culture of type M that has a maximum acidification rate of more than or equal to 0.05 units per hour but less than 0.15 pH units per hour in B-milk, wherein the culture of type M comprises one or more *Lactococcus lactis* ssp, *cremoris* strains selected from CHCC11552 deposited at the DSMZ under accession number DSM 26566; CHCC11583 deposited at the DSMZ under accession number DSM 26567; CHCC11603 deposited at the DSMZ under accession number DSM 26568; CHCC12085 deposited at the DSMZ under accession number DSM 26569; CHCC13347 deposited at the DSMZ under accession number DSM 26570, and mutants thereof;
(B) selecting a lactic acid bacteria culture of type R that has a maximum acidification rate of more than or equal to 0.40 pH units per hour in B-milk, and a maximum acidification rate of less than 0.05 pH units per hour in B-milk added 4% salt, wherein the culture of type R comprises one or more *Lactococcus lactis* ssp. *lactis* strains selected from CHCC10778 deposited at the DSMZ under accession number DSM 26564; CHCC11277 deposited at the DSMZ under accession number DSM 26565, and mutants thereof;
(C) optionally, selecting a lactic acid bacteria culture of type S that has a maximum acidification rate of more than or equal to 0.40 pH units per hour in B-milk and has a maximum acidification rate of more than 0.05 pH units per hour in B-milk added 4% salt, wherein the culture of type S comprises one or more of *Lactococcus lactic* ssp *cremoris* strain CHCC4421 deposited at the DSMZ under accession number DSM 26561, *Lactococcus lactis* ssp. *lactis* strain CHCC9673 deposited at the DSMZ under accession number DSM 26563, and mutants thereof;
(D) combining the cultures selected in (A), (B) and optionally (C); and
(E) packaging the combined cultures.

11. A method for preparing a soft cheese comprising, (a) adding to a milk substrate a lactic acid bacteria culture according to claim 1 and a coagulant.

12. The method of claim 11, wherein the lactic acid bacteria culture includes the lactic acid bacteria culture of type S, further comprising
(b) separating curd from whey; and
(c) adding a mold culture to the curd.

13. The method of claim 11, wherein the lactic acid bacteria culture is added in the form of a direct vat set culture.

14. The method of claim 12, wherein the mold culture is selected from *Penicillium* species.

* * * * *